United States Patent
Lee et al.

(10) Patent No.: US 11,735,317 B2
(45) Date of Patent: Aug. 22, 2023

(54) METHOD FOR GENERATING PREDICTION RESULT FOR PREDICTING OCCURRENCE OF FATAL SYMPTOMS OF SUBJECT IN ADVANCE AND DEVICE USING SAME

(71) Applicants: VUNO, INC., Seoul (KR); HYEWON MEDICAL FOUNDATION, Gyeonggi-do (KR)

(72) Inventors: Yeongnam Lee, Gyeonggi-do (KR); Yeha Lee, Gyeonggi-do (KR); Joonmyoung Kwon, Seoul (KR)

(73) Assignees: VUNO, INC., Seoul (KR); HYEWON MEDICAL FOUNDATION, Gyeonggi-do (KR)

( * ) Notice: Subject to any disclaimer, the term of this patent is extended or adjusted under 35 U.S.C. 154(b) by 492 days.

(21) Appl. No.: 16/638,250

(22) PCT Filed: Aug. 7, 2018

(86) PCT No.: PCT/KR2018/008918
§ 371 (c)(1),
(2) Date: Feb. 11, 2020

(87) PCT Pub. No.: WO2019/031794
PCT Pub. Date: Feb. 14, 2019

(65) Prior Publication Data
US 2020/0176117 A1  Jun. 4, 2020

(30) Foreign Application Priority Data

Aug. 11, 2017  (KR) .................. 10-2017-0102265
Aug. 23, 2017  (KR) .................. 10-2017-0106529

(51) Int. Cl.
*G16H 40/63*  (2018.01)
*G16H 50/30*  (2018.01)
(Continued)

(52) U.S. Cl.
CPC ........... *G16H 40/63* (2018.01); *G06F 18/217* (2023.01); *G06F 18/241* (2023.01); *G06N 3/084* (2013.01);
(Continued)

(58) Field of Classification Search
CPC .. G06F 18/217; G06F 18/241; G06F 18/2413; G06F 2218/12; G06N 3/044;
(Continued)

(56) References Cited

U.S. PATENT DOCUMENTS 8,668,644 B2     3/2014  Ong
2004/0078223 A1*  4/2004  Sacco ................... G16H 50/30
                                                                     705/2

(Continued)

FOREIGN PATENT DOCUMENTS

JP     H4-314430 A      11/1992
JP     2013-524865 A     6/2013
(Continued)

OTHER PUBLICATIONS

Gopalswamy et al. "Deep recurrent neural networks for predicting intraoperative and postoperative outcomes and trends." 2017 IEEE EMBS International Conference on Biomedical & Health Informatics (BHI). IEEE, Feb. 2017. (Year: 2017).*

(Continued)

*Primary Examiner* — Katrina R Fujita
(74) *Attorney, Agent, or Firm* — Nicholas Park

(57) ABSTRACT

The present invention relates to a method for generating a prediction result for predicting an occurrence of fatal symptoms of a subject in advance, a method for performing data classification by using data augmentation in mechanical learning for the same, and a computing device using the same. Particularly, the computing device according to the present invention acquires vital signs of the subject, converts (Continued)

the same into individuated data, generates analysis information from the individuated data on the basis of a machine learning model, generates a prediction result by referring to the analysis information, and provides the prediction result to an external entity.

13 Claims, 4 Drawing Sheets

(51) Int. Cl.
*G06N 20/20* (2019.01)
*G06N 20/10* (2019.01)
*G06N 3/084* (2023.01)
*G06F 18/21* (2023.01)
*G06F 18/241* (2023.01)

(52) U.S. Cl.
CPC .............. *G06N 20/10* (2019.01); *G06N 20/20* (2019.01); *G16H 50/30* (2018.01)

(58) Field of Classification Search
CPC ........ G06N 3/045; G06N 3/047; G06N 3/048; G06N 3/084; G06N 3/088; G06N 20/10; G06N 20/20; G16H 40/03; G16H 50/20; G16H 50/30
See application file for complete search history.

(56) References Cited

U.S. PATENT DOCUMENTS

| 2005/0182655 | A1* | 8/2005 | Merzlak | G16H 50/70 |
| | | | | 705/2 |
| 2011/0202486 | A1* | 8/2011 | Fung | G06B 40/20 |
| | | | | 706/46 |
| 2013/0151516 | A1* | 6/2013 | Park | G16H 50/70 |
| | | | | 707/736 |
| 2013/0185097 | A1* | 7/2013 | Saria | G06Q 10/00 |
| | | | | 705/3 |
| 2013/0237776 | A1* | 9/2013 | Ong | A61B 5/01 |
| | | | | 600/301 |
| 2016/0012192 | A1* | 1/2016 | Radhakrishnan | G16H 10/60 |
| | | | | 706/12 |
| 2016/0143594 | A1 | 5/2016 | Moorman et al. | |
| 2016/0364544 | A1* | 12/2016 | Das | A61B 5/02055 |
| 2016/0364545 | A1* | 12/2016 | Das | G16H 50/70 |
| 2017/0147777 | A1* | 5/2017 | Kim | G16H 50/30 |
| 2018/0004901 | A1* | 1/2018 | Avinash | G16H 50/30 |
| 2019/0139631 | A1* | 5/2019 | Eshelman | G16H 20/00 |
| 2020/0176114 | A1* | 6/2020 | Badawi | G16H 50/20 |

FOREIGN PATENT DOCUMENTS

| KR | 10-2013-0082551 | 7/2013 |
| KR | 10-2014-0108417 | 9/2014 |
| KR | 10-2017-0061222 | 6/2017 |

OTHER PUBLICATIONS

Desautels et al. "Prediction of sepsis in the intensive care unit with minimal electronic health record data: a machine learning approach." JMIR medical informatics 4.3 (2016): e5909. (Year: 2016).*

Prince, John. Vital-Sign Monitoring Using Pulse Oximetry for Automated Triage and the Prediction of Patient Deterioration. Diss. Tese. Doutorado em Filosofia,. Universidade de Oxord: Trinity, 2016. (Year: 2016).*

Tran, Luan et al., Disentangled Representation Learning GAN for Pose-Invariant Face Recognition, Jul. 2017, pp. 5-6, IEEE Computer Vision and Pattern Recognition (CVPR 2017).

Odena, Augustus et al., Conditional Image Synthesis With Auxiliary Classifier GANs, Oct. 30, 2016, pp. 3, arXiv.org.

Goodfellow, I. J. et al., NIPS'14, Proceedings of the 27th International Conference on Neural Information Processing Systems, vol. 2, Dec. 2014, pp. 2672-2680.

Miningoo, Typical techniques of normalization: z-score normalization and min-max normalization, Oct. 26, 2016, URL:https://miningoo.com/1032.

Office Action Issued by Japan Patent Office for JP2020-530296 dated Mar. 16, 2021.

Office Action for the Japanese Patent Application No. 2021-127878 issued by the Japanese Patent Office dated Sep. 20, 2022.

* cited by examiner

METHOD FOR GENERATING PREDICTION RESULT FOR PREDICTING OCCURRENCE OF FATAL SYMPTOMS OF SUBJECT IN ADVANCE AND DEVICE USING SAME

CROSS-REFERENCE TO RELATED APPLICATION

This application is a national stage application of PCT/KR2018/008918 filed on Aug. 7, 2018, which claims priority of Korean patent application numbers 10-2017-0102265 filed on. Aug. 11, 2017 and 10-2017-0106529 filed on Aug. 23, 2017. The disclosure of each of the foregoing applications is incorporated herein by reference in its entirety.

TECHNICAL FIELD

Example embodiments relate to a method of generating a prediction result for early predicting an occurrence of fatal symptoms of a subject, a method of classifying data using data augmentation for machine learning, and a computing apparatus using the methods.

RELATED ART

In medical clinical trials, an occurrence of fatal of a subject, for example, a patient, such as cardiac arrest and sepsis, may significantly decrease survival discharge. For example, cardiac arrest accounts for 20 to 30% of survival discharge rates. Since such cardiac arrest has a change in vital signs before its occurrence, early prediction thereof is possible. However, a prediction method according to the related art mainly depends on experience or knowledge of a medical specialist, for example, a nurse or a doctor in charge. Therefore, the risk of the subject or the patient may be evaluated quiet differently depending on an individual's capability. Also, there is a shortage of emergency medical staff for such an evaluation itself.

Briefly describing the prediction method according to the related art, the risk of fatal symptoms, such as cardiac arrest, is determined by assigning scores according to a conventional rule-based vital sign value. Here, there is a high rate of false negative or false positive. Here, the false negative refers to a case of not predicting the risk of a patient: of which actual fatal symptoms are to occur and the false positive refers to a case of predicting an occurrence of actual fatal symptoms even though the fatal symptoms do not occur.

In reality, an imbalance of data becomes an issue in classifying a class of data through a machine learning.

For example, a case of predicting cardiac arrest of a patient corresponds to a 2-class classification in which a series of vital signs acquired from the patient are classified into vital signs (first class) corresponding to cardiac arrest or classified into vital signs (second class) of a normal patient not having cardiac arrest, through a machine learning using the series of vital signs as learning data. However, since many subjects are subjects not showing corresponding symptoms, vital sign data corresponding to cardiac arrest are few. That is, a severe class imbalance of learning data occurs.

That is, a machine learning algorithm performs learning with a set of data biased to one class and thus, a resulting classification model may decrease an overall accuracy and may further decrease an accuracy of classifying data corresponding to the other class. In a classification, it is important to match a class (a minority class, the first class in the above example) to which a minority of data belongs as well as a class (a majority class, the second class in the above example) to which a majority of data belongs. Therefore, the aforementioned issue needs to be outperformed.

Accordingly, proposed herein is a fatal symptoms early prediction result generating method that may early predict fatal symptoms further accurately compared to a conventional method. Also, to this end, there is proposed a method of improving a conventional GAN as a method of increasing an accuracy of a classification model through a machine learning by generating data similar to true data, that is, by performing an effective data augmentation as a method of overcoming a severe class imbalance of data.

(Reference document) Non-patent document 1: Goodfellow, Ian J.; Pouget-Abadie, Jean; Mirza, Mehdi; Xu, Bing; Warde-Farley, David; Ozair, Sherjil; Courville, Aaron; Bengio, Yoshua (2014). "Generative Adversarial Networks"

DETAILED DESCRIPTION

Technical Subject

Example embodiments are to detect a patient with imminent fatal symptoms, such as cardiac arrest, and to increase a survival rate of the patient by reducing existing high false negatives.

Also, example embodiments are to increase an accuracy of a classification model through existing machine learning using data augmentation of generating a minority class of learning data similar to true data although a class imbalance of learning data is high in machine learning.

Also, example embodiments are to improve medical treatment conditions by saving unnecessary consultation hours through a decrease in existing high false positives.

Solution

Characteristic constitutions of this disclosure to accomplish the aforementioned objectives and to achieve characteristic effects of the disclosure are as follows:

According to an aspect of example embodiments, there is provided a method of generating a prediction result for early predicting an occurrence of fatal symptoms of a subject, the method including: (a) acquiring, by a computing apparatus, or supporting another apparatus interacting with the computing apparatus to acquire vital signs of the subject; (b) converting, by the computing apparatus, or supporting the other apparatus to convert the acquired vital signs to individuation data that is data individuated for the subject; (c) generating, by the computing apparatus, or supporting the other apparatus to generate analysis information about an early prediction of the fatal symptoms from the individuation data based on a machine learning model for the early prediction of the fatal symptoms, and generating or supporting the other apparatus to generate the prediction result as a result of predicting the occurrence of the fatal symptoms during a duration from a point in time t corresponding to a single specific vital sign among the vital signs to a point in time t+n that is a point in time after a desired time interval n by referring to the generated analysis information; and (d) providing, by the computing apparatus, or supporting the other apparatus to provide the generated prediction result to an external entity.

Desirably, the method may further include (e) updating, by the computing apparatus, or supporting the other apparatus to update the machine learning model based on evaluation information about the prediction result.

According to another aspect of example embodiments, there is provided a computing apparatus for generating a prediction result for early predicting an occurrence of fatal symptoms of a subject, the computing apparatus including: a communicator configured to acquire vital signs of the subject; and a processor configured to convert or support another apparatus interacting through the communicator to convert the acquired vital signs to individuation data that is data individuated for the subject. The processor is configured to generate or support the other apparatus to generate analysis information about an early prediction of the fatal symptoms from the individuation data based on a machine learning model for the early prediction of the fatal symptoms, generate or support the other apparatus to generate the prediction result as a result of predicting the occurrence of the fatal symptoms during a duration from a point in time t corresponding to a single specific vital sign among the vital signs to a point in time t+n that is a point in time after a desired time interval n by referring to the generated analysis information, and provide the generated prediction result to an external entity.

Desirably, the processor may be configured to update or support the other apparatus to update the machine learning model based on evaluation information about the prediction result.

According to another aspect of example embodiments, there is provided a method of classifying data using data augmentation for a machine learning, the method including: (a) acquiring, by a computing apparatus, or supporting another apparatus interacting with the computing apparatus to acquire true data; (b) training, by the computing apparatus, or allowing the other apparatus to train a generator and a discriminator of a modified generative adversarial network (GAN) based on information of a label corresponding to the acquired true data and the true data, wherein, in the modified GAN, the generator includes a sub-generator configured to generate similar data corresponding to each of a plurality of labels, the sub-generator is configured to generate similar data belonging to a label corresponding to the sub-generator, and the discriminator is configured to predict a specific label that is a label corresponding to data to be discriminated by the discriminator among the plurality of labels; (c) training, by the computing apparatus, or allowing the other apparatus to train a machine learning model by generating the similar data using the trained modified GAN and by using (i) the true data and the similar data or (ii) the similar data as learning data of a predetermined machine learning model for classification; and (d), in response to acquiring data to be classified, generating, by the computing apparatus, or supporting the other apparatus to generate classification information of the data to be classified by classifying the data to be classified based on the trained machine learning model. For example, the machine learning model for classification may use data generated by the generator of the modified GAN trained based on true data as learning data.

According to another aspect of example embodiments, there is provided a computing apparatus for classifying data using data augmentation for a machine learning, the computing apparatus including: a communicator configured to acquire true data; and a processor configured to train or allow another apparatus interacting through the communicator to train a generator and a discriminator of a modified generative adversarial network (GAN) based on information of a label corresponding to the acquired true data and the true data, wherein, in the modified GAN, the generator includes a sub-generator configured to generate similar data corresponding to each of a plurality of labels, the sub-generator is configured to generate similar data belonging to a label corresponding to the sub-generator, and the discriminator is configured to predict a specific label that is a label corresponding to data to be discriminated by the discriminator among the plurality of labels. The processor is configured to train or allow the other apparatus to train a machine learning model by generating the similar data using the trained modified GAN and by using (i) the true data and the similar data or (ii) the similar data as learning data of a predetermined machine learning model for classification, and, in response to acquiring data to be classified, generate or support the other apparatus to generate classification information of the data to be classified by classifying the data to be classified based on the trained machine learning model.

According to another aspect of example embodiments, there is provided a computer program stored in media including instructions that cause a computing apparatus to perform the method.

Effects

According to some example embodiments, compared to an existing method of determining the risk of a patient depending on experience or knowledge of medical specialists, it is possible to further quickly and easily predict fatal symptoms, such as cardiac arrest, sepsis, etc.

Also, according to some example embodiments, compared to an existing method of assigning a rule-based score, it is possible to further decrease false negatives and false positives in predicting fatal symptoms.

Also, according to some example embodiments, it is possible to innovate a workflow in a medical field by enabling a continuous prediction in time-series clinical processes.

Also, according to some example embodiments, a prediction performance may be continuously improved by using a method of this disclosure.

Also, according to some example embodiments, it is possible to outperform a class imbalance of learning data that is an issue in a classification model by existing machine learning, that is, in training a machine learning model for classification, through a data augmentation of learning data.

For example, a data classification method using data augmentation according to example embodiments may apply to many medical determination situations and thus, may enhance a low accuracy of a classification model caused by minority data related to cardiac arrest, sepsis, etc., since most subjects are subjects not showing corresponding symptoms.

BRIEF DESCRIPTION OF DRAWINGS

Example embodiments will be described in more in detail with reference to the following figures that are simply a portion of the example embodiments and those of ordinary skill in the art (hereinafter, "those skilled in the art") to which this disclosure pertains may readily acquire other figures based on the figures without an inventive work being made.

Figure 1:
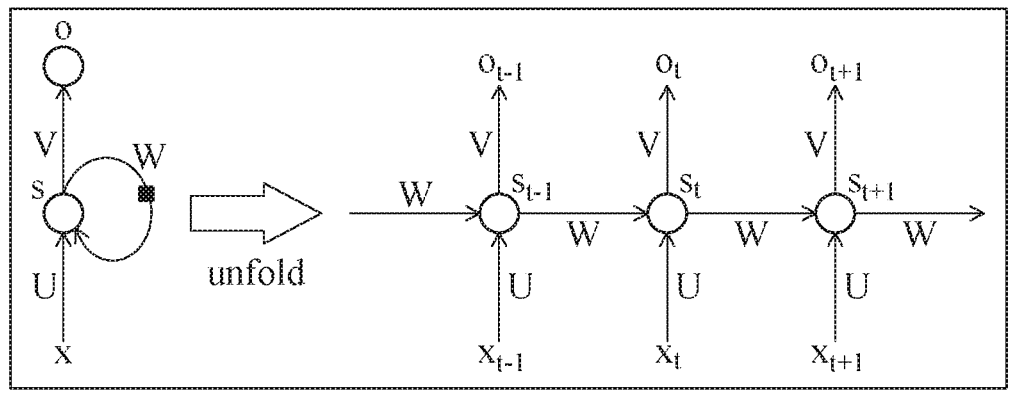
FIG. 1 illustrates an example of describing a recurrent neural network (RNN) that is a machine learning model according to an example embodiment.

The following detailed description of this disclosure is described with reference to the accompanying drawings in which specific example embodiments of the disclosure are illustrated as examples, to fully describe purposes, technical solutions, and advantages of the disclosure. The example embodiments are described in detail enough for those skilled in the art to carry out the disclosure.

The term "fatal symptoms" when used in the detailed description and claims and modifications thereof are not limited to cardiac arrest that is one example of targets to which the disclosure applies and should be understood as a concept including any kind of clinical phenomena that may cause a great risk in a subject's life due to time series changes, such as sepsis, etc.

Also, the term "vital signs" when used in the detailed description and claims should not be interpreted to be limited to a general meaning of a measurement value, such as a body temperature, an electrocardiogram (ECG), a respiration, a pulse rate, a blood pressure, an oxygen saturation, a skin conductivity, and the like, of a subject and should be understood to include electroencephalography (EEG) signals, an amount of specific substance among biological samples acquirable through other measurements, a concentration, and the like.

Here, "biological samples" should be understood as various kinds of substances that may be collected from the subject, for example, blood, serum, urine, lymph, cerebrospinal fluid, saliva, semen, vaginal fluid, etc., of the subject.

The term "training/learning" when used in the detailed description and claims refers to performing a machine learning through computing according to a procedure and can be understood by those skilled in the art that the term is not intended to refer to mental acts, such as human educational activities.

Also, the terms "comprises/includes" when used in the detailed description and claims and modifications thereof are not intended to exclude other technical features, additions, components, or operations. Those skilled in the art may clearly understand a portion of other purposes, advantages, and features of the disclosure from this specification and another portion thereof from implementations of the disclosure. The following examples and drawings are provided as examples only and not to limit the disclosure.

Further, the disclosure may include any possible combinations of example embodiments described herein. It should be understood that, although various example embodiments differ from each other, they do not need to be exclusive. For example, a specific shape, structure, and feature described herein may be implemented as another example embodiment without departing from the spirit and scope of the disclosure. Also, it should be understood that a position or an arrangement of an individual component of each disclosed example embodiment may be modified without departing from the spirit and scope of the disclosure. Accordingly, the following detailed description is not to be construed as being limiting and the scope of the disclosure, if properly described, is limited by the claims, their equivalents, and all variations within the scope of the claims. In the drawings, like reference numerals refer to like elements throughout.

Unless the context clearly indicates otherwise, the singular forms "a", "an", and "the", are intended to include the plural forms as well. Also, when description related to a known configuration or function is deemed to render the present disclosure ambiguous, the corresponding description is omitted.

Hereinafter, example embodiments of the disclosure are described in detail with reference to the accompanying drawings such that those skilled in the art may easily perform the example embodiments.

FIG. 1 illustrates an example of describing a recurrent neural network (RNN) that is a machine learning model according to an example embodiment.

Referring to FIG. 1, in a machine learning model used herein, a deep neural network model may be briefly described to be in a form in which artificial neural networks are stacked in multiple layers. That is, a deep structured neural network may be represented as a deep neural network or a DNN that is a network in a deep structure, and, referring to FIG. 1, may be trained using a method of automatically learning features of vital signs and a relationships between the vital signs through learning of a large amount of data in a structure that includes a multilayered network and, through this, reducing an error of an objective function, that is, a prediction accuracy of fatal symptoms. It is also expressed as a concatenation between nerve cells of the human brain and the deep neural network (DNN) is becoming a next generation model of artificial intelligence (AI).

Among DNN models used herein, a recurrent neural network (RNN) may be used to analyze sequentially input data as shown in FIG. 1. The RNN model is in a structure to detect a feature of data according to a time sequence and to selectively apply a main feature to be referred to when analyzing a current point in time among features of previous points in times. For example, referring to FIG. 1, when analyzing data input at a point in time t+1, the data may be analyzed by learning main features analyzed at points in times t−1 and t. As described above, according to example embodiments, it is possible to extract a change in vital signs over time using a structure of the RNN and to use the extracted change for prediction of fatal symptoms.

For example, the RNN unfolded according to time-series order, time flow, or time axis may be understood as a DNN having an infinite number of layers. In FIG. 1, $x_t$ denotes an input vector at the point in time t and $s_t$ denotes a hidden state (i.e., memoir of a neural network) at the point in time t.

Describing again, the RNN of FIG. 1 follows $s_t=f(Ux_t+Ws_{t-1})$ and $y=g(Vs_t)$. For reference, y is indicated with o in FIG. 1. Here, f denotes an activation function (e.g., tank( ) and ReLU function) and U, V, and W denote parameters of a neural network. Here, U, V, and W refer to parameters that are shared equally across stages of all of the points in times in the RNN, which differs from those in a feedforward neural network. Also, g denotes an activation function (typically, a softmax function) for an output layer, and y denotes an output vector of the neural network at the point in time t. A method using the RNN according to an example embodiment is further described below.

Figure 2:
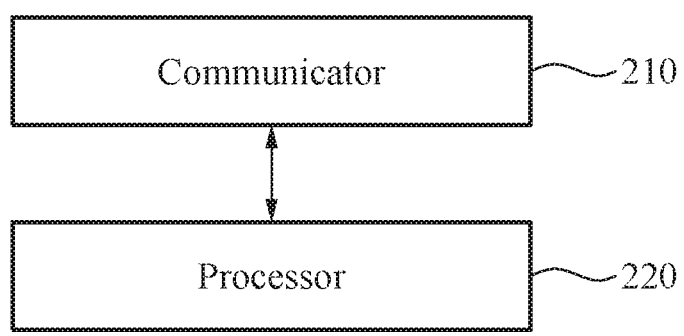
FIG. 2 is a diagram illustrating an example of a computing apparatus configured to perform a method of generating a prediction result for early predicting an occurrence of fatal symptoms of a subject (hereinafter, also referred to as a "fatal symptoms early prediction result generating method") and a method of classifying data using a data augmentation (hereinafter, also referred to as a "data classification method") according to an example embodiment.

FIG. 2 is a diagram illustrating an example of a computing apparatus configured to perform a fatal symptoms early prediction result generating method according to an example embodiment.

Referring to FIG. 2, a computing apparatus 200 according to an example embodiment includes a communicator 210 and a processor 220, and may directly or indirectly communicate with an external computing apparatus (not shown) through the communicator 210.

In detail, the computing apparatus 200 may achieve a desired system performance using a combination of typical computer hardware an apparatus including a computer processor, a memory, a storage, an input device and an output device, components of other existing computing apparatuses, etc.; an electronic communication apparatus such as a router, a switch, etc.; an electronic information storage system such as a network attachment storage (NAS) and a storage area network (SAN)) and computer software (i.e., instructions that enable a computing apparatus to function in a specific manner).

The communicator 210 of the computing apparatus 200 may transmit and receive a request and a response with another interacting computing apparatus. As an example, the request and the response may be implemented using the same transmission control protocol (TCP) session. However, it is provided as an example only. For example, the request: and the response may be transmitted and received as a user datagram protocol (UDP) datagram. In addition, in a broad sense, the communicator 210 may include a keyboard, a mouse, and other external input devices to receive a command or an instruction, etc.

Also, the processor 220 of the computing apparatus 200 may include a hardware configuration, such as a data bus, a micro processing unit (MPU) or a central processing unit (CPU), a cache memory, and the like. Also, the processor 220 may further include a software configuration of an application that performs a specific object, an operating system (OS), and the like.

Figure 3:
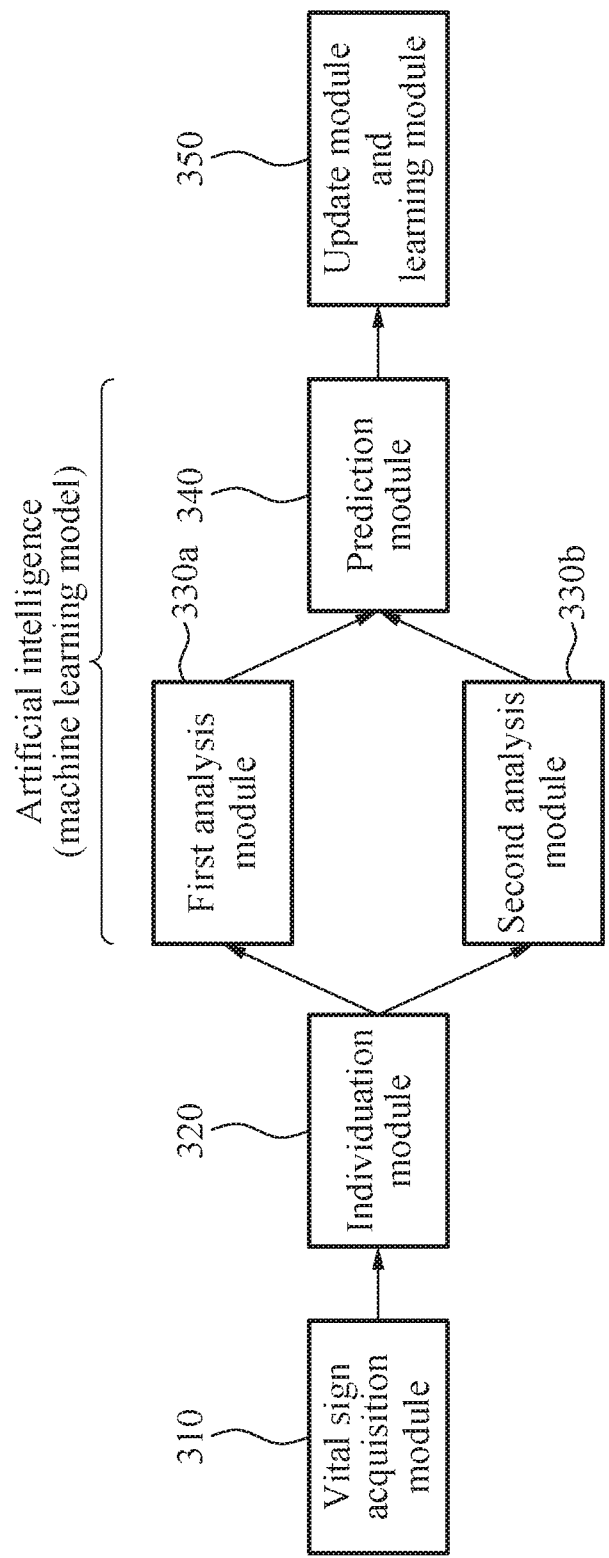
FIG. 3 is a diagram illustrating an example of hardware and software architectures of a computing apparatus configured to perform a fatal symptoms early prediction result generating method according to an example embodiment.

FIG. 3 is a diagram illustrating an example of hardware and software architectures of a computing apparatus configured to perform a fatal symptoms early prediction result generating method according to an example embodiment.

Describing a method and a configuration of an apparatus according to an example embodiment with reference to FIG. 3, the computing apparatus 200 may include a vital sign acquisition module 310 as a component. Those skilled in the art may understand that the vital sign acquisition module 310 may be implemented through an interaction with the communicator 210 included in the computing apparatus 200, or an interaction between the communicator 210 and the processor 220.

The vital sign acquisition module 310 may acquire vital signs of a subject. For example, vital signs may be acquired from an electronic medical record (EMR) of the subject. However, it is provided as an example only.

The acquired vital signs may be forwarded to an individuation module 320. The individuation module 320 converts the vital signs to individuation data that is data individuated or personalized for the subject. For example, the vital signs may be acquired from the subject that is a human (*Homo sapiens*). However, those skilled in the art may understand that they are not limited thereto. That is, "individuation" may be performed with respect to a specific animal subject in correspondence to performing "personalization" with respect to a specific human subject.

Such conversion is performed since a normal vital sign differs from a vital sign just before an occurrence of fatal symptoms for each subject. For example. One subject may breathe 45 times per minute when normal, while another subject may breathe 45 times just before cardiac arrest. As described above, the acquired vital signs need to be modified to fit an individual subject instead of being simply used.

As an example of the conversion to individuate vital signs for the subject if necessary, the individuation module 320 may convert: the vital signs to the individuation data by calculating a deviation of vital signs of an entire time duration by subtracting an average of vital signs of an initial desired time duration among the vital signs from the vital signs of the entire time duration and by calculating a standard score (z-score) of the vital signs of the entire time duration of the subject as the individuation data by referring to an average and a variance of vital signs of a plurality of other subjects.

Further describing in detail, with the assumption that vital signs of first 10 hours of a subject are normal, a difference from an average, that is, a deviation may be calculated using a value acquired by subtracting an average of the vital signs of the 10 hours from vital signs of remaining hours. A z-score for the entire vital signs of the subject may be acquired by calculating an average and a variance of vital signs with respect to all of the subjects. In this manner, a subsequent vital sign may be considered as a value relatively deviated from normal vital signs of each subject rather than using an absolute value.

When the individuation data that is data individuated for each subject is input to a first analysis module 330a and a second analysis module 330b, analysis information about the early prediction may be generated. A prediction module 340 may generate a prediction result about an occurrence probability of fatal symptoms by a specific point in time based on the analysis information. A process of generating the analysis information and the prediction result is further described below.

An update module and learning module 350 may function to pretrain a machine learning model to be used in response to an occurrence of fatal symptoms of the subject by performing the method according to the example embodiments or to update the machine learning model based on evaluation information about the prediction result according to performing of the method.

Figure 4:
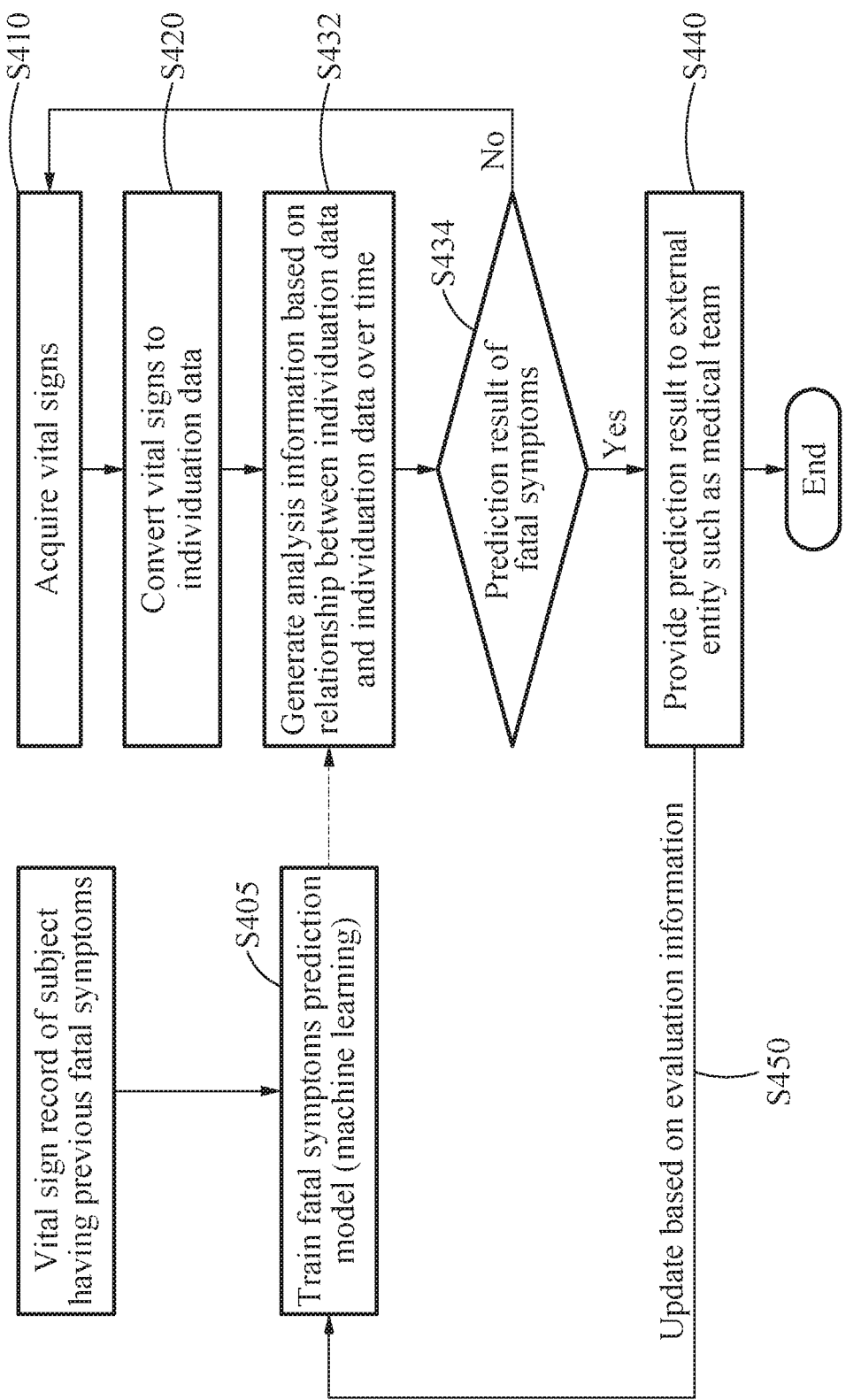
FIG. 4 is a flowchart illustrating an example of a fatal symptoms early prediction result generating method according to an example embodiment.

Hereinafter, a method of generating a result of early predicting fatal symptoms according to an example embodiment is described with reference to FIG. 4. FIG. 4 is a flowchart illustrating an example of a fatal symptoms early prediction result generating method according to an example embodiment.

Referring to FIG. 4, a prediction result generating method according to an example embodiment includes operation S410 of acquiring, by the vital sign acquisition module 310 implemented by the communicator 210 of the computing apparatus 200, vital signs of the subject. For example, the vital signs may be time series vital signs from a point in time t0 to a point in time t. However, without being limited thereto, the vital signs may be vital signs at a single point in time. Those skilled in the art may understand from this specification that a prediction result about fatal symptoms may be generated even with respect to vital signs at a single point in time.

Referring to FIG. 4, the prediction result generating method further includes operation S420 of converting, by the individuation module 320 implemented by the processor 220 of the computing apparatus 200, or supporting another apparatus interacting through the communicator 210 to convert the acquired vital signs to individuation data that is data individuated for the subject.

According to an example embodiment, as described above, in operation S420, the individuation module 320 may calculate a deviation of vital signs of an entire time duration by subtracting an average of vital signs of an initial desired time duration among the vital signs from the vital signs of the entire time duration, and may calculate a standard score (z-score) of the vital signs of the entire time duration of the subject as the individuation data by referring to an average and a variance of vital signs of a plurality of other subjects. Here, those skilled in the art may understand that a method of generating individuation data by converting to fit a characteristic of a patient for each subject is not limited to the aforementioned method.

Referring again to FIG. 4, the fatal symptoms early prediction result generating method further includes operation S432 of generating or supporting the other apparatus to generate analysis information about an early prediction of the fatal symptoms from the individuation data based on a machine learning model for the early prediction of the fatal symptoms and operation S434 of generating or supporting the other apparatus to generate the prediction result as a result of predicting the occurrence of the fatal symptoms during a duration from a point in time t corresponding to a single specific vital sign among the vital signs to a point in time t+n that is a point in time after a desired time interval n by referring to the generated analysis information.

According to an example embodiment, a recurrent neural network (RNN) model may be included as an analysis model in the machine learning model. The analysis modules 330a and 330b that implement the analysis model may be executed by the processor 220. As described above, the RNN model follows $s_t=f(Ux_t+Ws_{t-1})$ and $y=g(Vs_t)$. Here, the $x_t$ denotes the individuation data that is an input vector at the point in time t or a value processed from the individuation data. Here, the value processed from the individuation data may refer to, for example, a variance (from a previous point in time to a current point in time) of the individuation data or an amount of change in the variance.

Also, the $s_t$ denotes a hidden state corresponding to a memory of the RNN model at the point in time t, the $s_{t-1}$ denotes the hidden state at the point in time t−1, the U, V, and W denote neural network parameters shared equally across all the points in times of the RNN model, the f denotes a predetermined first activation function that is selected to calculate the hidden state, the y denotes an output layer that is a latent feature according to the RNN model at the point in time t as the analysis information, and the g denotes a predetermined second activation function that is selected to calculate the output layer.

In detail, the first analysis module 330a between the analysis modules 330a and 330b functions to apply a relationship between the individuation data by referring to individuation data at the point in time t, and may correspond to, for example, $Ux_t$ in the RNN model. Also, the second analysis module 330b between the analysis modules 330a and 330b functions to apply a change in the individuation data over time by referring to individuation data up to the point in time t−1 and may correspond to, for example, $Ws_{t-1}$ in the RNN model.

Here, the first activation function f may be a tanh( ) or ReLU function generally used. Also, the second activation function g may be a softmax function generally used. The first activation function and the second activation function may be selectively applied based on each purpose and complexity of calculation.

Also, according to the example embodiment, the machine learning model may further include a second neural network model including at least one fully connected layer for calculating an occurrence probability of the fatal symptoms from the output layer (y) as at least a portion of a prediction model. The prediction module 340 that implements the prediction model may be executed by the processor 220.

Prior to performing the fatal symptoms early prediction result generating method according to example embodiments, operation S405 of pretraining the machine learning model may be required. To this end, an updating and learning module 350, or the learning module may be executed by the processor 220.

For learning of the RNN model, the updating and learning module 350 may train the RNN model through backpropagation through time (BPTT) of using individual individuation data for a plurality of existing subjects as learning data. Through this, the U, V and W may be determined.

Also, for learning of the second neural network model, the updating and learning module 350 may train the second neural network model through backpropagation of using individual individuation data for a plurality of existing subjects and an occurrence/non-occurrence of fatal symptoms at each point in time of the existing subjects as learning data.

Further describing operations S432 and S434 according to the example embodiment, the processor 220 may acquire or support the other apparatus to acquire the output layer at the point in time t+n as the analysis information by using the individuation data or the value processed from the individuation data as an input of the analysis modules 330a and 330b in operation S432. In operation S434, the processor 220 may generate or support the other apparatus to generate an occurrence probability of the fatal symptoms up to the point in time t+n as the prediction result by using the output layer at the point in time t+n as an input of the prediction module 340.

Referring again to FIG. 4, the prediction result generating method further includes operation S440 of providing, by the processor 220, the generated prediction result to an external entity. Here, the external entity may include a user of the computing apparatus 200, an administrator, a medical specialist in charge of the subject, and the like. In addition thereto, any entity capable of acquiring the prediction result should be understood to be included.

Meanwhile, similar to the example embodiment of FIG. 4, when the occurrence probability of the fatal symptoms is predicted to be higher than a predetermined probability, the prediction result may be provided to the external entity.

The fatal symptoms early prediction result generating method according to example embodiments may provide the prediction result about the fatal symptoms based on the pretrained machine learning model. If evaluation information about the prediction result is used as data to retrain the machine learning model, the machine learning model may perform a further accurate prediction. Therefore, the prediction result generating method according to example embodiments may further include operation S450 of updating, by the processor 220, or supporting the other apparatus to update the machine learning model based on evaluation information about the prediction result. Here, individuation data (acquired from vital signs) not used for previous learning may be further considered and an error found in the previous learning ay be corrected. Therefore, the accuracy of the machine learning model may be enhanced. As data accumulates, the performance of machine learning continues to improve.

Here, the evaluation information about the prediction result may be provided from the external entity, such as the medical specialist, etc.

Such update refers to proceeding with learning again based on newly provided data and thus, may be substantially identical to the aforementioned operation S405. That is, the analysis model and the prediction model using the analysis modules 330a and 330b and the prediction module 340 are modified by considering the accuracy of prediction based on the evaluation information about the prediction result. In more detail, parameters, for example, the U, V, W, etc., used for the analysis model and the prediction model are modified.

The example embodiments may further quickly and conveniently predict fatal symptoms compared to a conventional method of predicting fatal symptoms, such as cardiac arrest, sepsis, etc., generally depending on experience or knowledge of medical specialists.

Advantages of the example embodiments described herein may significantly reduce burden of medical specialists in busy medical clinical conditions that they need to make an accurate determination and prediction based on a large amount of diagnostic data a day. Using technology based on machine learning, particularly, a deep neural network (DNN), the risk of a patient related to fatal symptoms acquired by a doctor only after years of training may be analyzed and learned using a computing apparatus itself based on a large amount of learning data. Accordingly, assistance may be made to determine cases that a human medical specialist may overlook or cases in which it is difficult to predict fatal symptoms. For example, according to the example embodiments, only patients of which fatal symptoms are suspected to occur based on the automatically generated prediction information, for example, by a predetermined point in time may be screened and medical staff may need to verify the screened patients. Accordingly, it is possible to improve the accuracy and speed of prediction of fatal symptoms.

Figure 5:
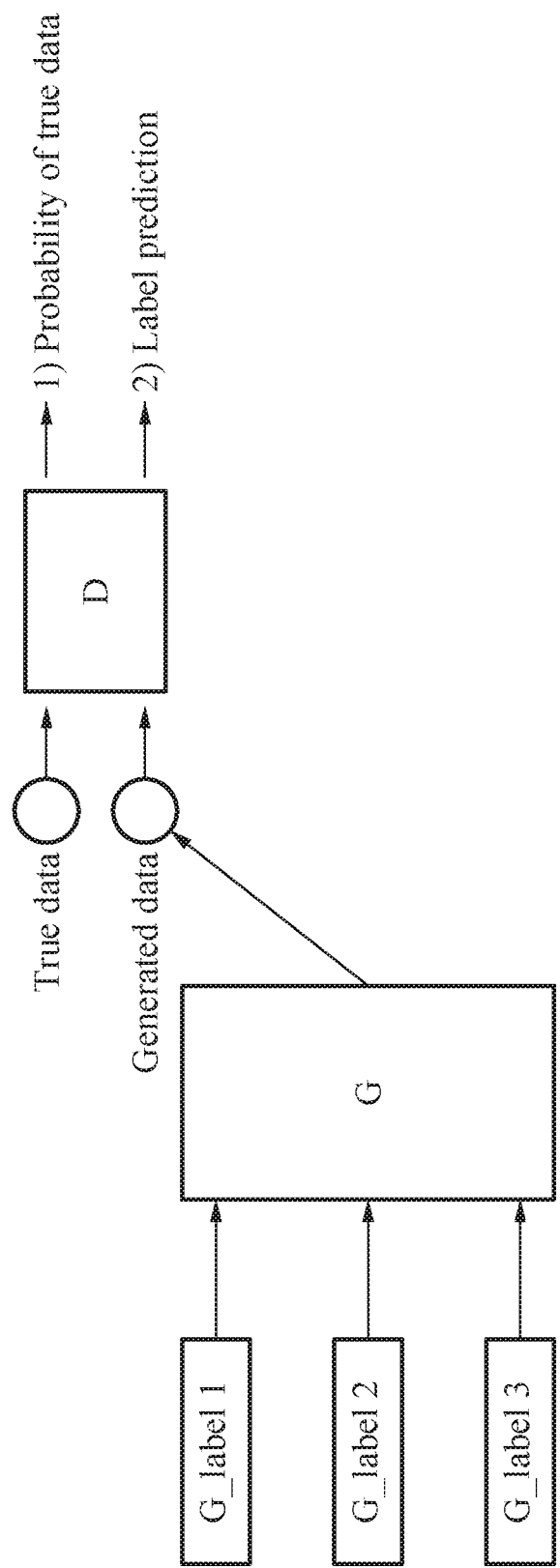
FIG. 5 illustrates an example of a method of performing a data augmentation using a modified generative adversarial network (GAN) according to an example embodiment.

FIG. 5 illustrates an example of a method of performing a data augmentation using a modified generative adversarial network (GAN) according to an example embodiment.

The example embodiment relates to outperforming a class imbalance issue found in the conventional machine learning, that is, to enhancing a reliability and accuracy of a machine learning model since the conventional machine learning is performed mainly based on data belonging to a majority class due to a class imbalance.

To this end, in the example embodiment, the following data augmentation may be performed. Referring to FIG. 5, the modified GAN according to the example embodiment may include a generator (indicated with 'G') configured to generate vital signs of fatal symptoms similar to reality and a discriminator (indicated with 'D') configured to discriminate true data from generated data.

In detail, according to the paper regarding the conventional GAN, non-patent document 1: [Goodfellow, Ian J.; Pouget-Abadie, Jean; Mirza, Mehdi; Xu, Bing; Warde-Farley, David; Ozair, Sherjil; Courville, Aaron; Bengio, Yoshua (2014). "Generative Adversarial Networks"], a generator is configured to generate data similar to true data to deceive a discriminator, such that the discriminator may determine the similar data as the true data, and the discriminator is configured to discriminate the true data from the generated similar data. During progress of learning by the GAN, each of the generator and the discriminator updates a network weight to achieve each corresponding purpose. Accordingly, after sufficient learning, the generator may generate data similar to true data and a discrimination rate by the discriminator may converge theoretically to 0.5.

Accordingly, since the generator sufficiently trained through the conventional GAN may generate data close to true data, the aforementioned class imbalance issue of data may be overcome by using the similar data generated by the generator of the conventional GAN as learning data for training the machine learning model.

The conventional GAN focuses on learning simply depending whether the input data is true data or fake data. Thus, if the input data may belong to various labels, the conventional GAN may not readily verify a label corresponding to the input data among the various labels.

To outperform the above limit, the modified GAN modified from the conventional GAN is used herein. Therefore, various kinds (i.e., kinds classified by labels) of data may be generated and determined by further considering information of a label related to data using the modified GAN.

In detail, dissimilar to the conventional GAN, the generator of the modified GAN may include sub-generators (indicated with 'G_label1', 'G_label2', and 'G_label3' in FIG. 5) each configured to generate similar data corresponding to a plurality of labels, respectively. Each sub-generator generates similar data belonging to a label corresponding to the sub-generator.

Also, dissimilar to the conventional GAN, the discriminator of the modified GAN predicts and discriminates a label corresponding to data to be determined by the discriminator instead of simply determining whether the data to be determined by the discriminator is true data or fake da a.

For example, such labels may include 'cardiac arrest group', 'sepsis group', 'normal', and the like. Therefore, the modified GAN according to example embodiment may support data generated by the generator to become similar data close to true data, and may support the discriminator to verify a label corresponding to the true data or the similar data input to the discriminator, such that the generator may generate a specific label through the sub-generator.

That is, the modified GAN according to the example embodiment may be trained based on true data and a kind of a label corresponding to the true data and accordingly, may generate various kinds of similar data classified by labels to be close to true data. In particular, with respect to a specific label having a relatively small quality of true data, the modified GAN may replenish an insufficient quantity by generating similar data corresponding to the specific label and thereby solve a data imbalance issue about the specific label.

Hereinafter, a data classification method according to an example embodiment is described based on the aforementioned description. The data classification method includes operation S100' of acquiring, by the computing apparatus 200 through the communicator 210, or supporting another apparatus interacting with the computing apparatus 200 to acquire true data. For example, such true data may be a time series signal, however, without being limited thereto, any data to be classified may be included in the true data.

The data classification method further includes operation S200' of training, by the computing apparatus 200 through the processor 210, or allowing the other apparatus interacting through the communicator 210 to train the generator and the discriminator of the modified GAN based on label information of a label corresponding to the acquired true data and the true data. A difference between the modified GAN and the conventional GAN is described above and further description is omitted.

The data classification method further includes operation S300' of training, by the computing apparatus 200 through the processor 220, or allowing the other apparatus to train the machine learning model by generating the similar data using the trained modified GAN and by using (i) the true data and the similar data or (ii) the similar data as learning data of a predetermined machine learning model for classification.

For example, a convolutional neural network (CNN), a recurrent: neural network (RNN), and the like may be included in the machine learning model. However, it is provided as an example only, which may be understood by those skilled in the art.

Also, the data classification method further includes operation S400' of, in response to acquiring data to be classified by the communicator 210 of the computing apparatus 200, generating, by the computing apparatus 200 through the processor 220, or supporting the other apparatus to generate classification information of the data to be classified by classifying the data to be classified based on the machine learning model.

Further, the data classification method may further include operation. S500' of providing, by the computing apparatus 200 through the processor 220, or supporting the other apparatus to provide the classification information to an external entity. Here, the external entity may include a user of the computing apparatus, an administrator, and the like. In addition thereto, it should be understood that any entity having a right to acquire the classification information may be included.

Also, the data classification method may further include operation S600' of updating, by the computing apparatus 200, or supporting the other apparatus to update the machine learning model based on evaluation information about an accuracy of the classification information.

The aforementioned data classification method according to the example embodiment may provide classification information about data to be classified based on a predetermined machine learning model. Therefore, in the case of using evaluation information about an accuracy of classification information as retraining data, a further accurate prediction may be performed. Accordingly, the data classification method may further include operation S600' of updating, by the computing apparatus 200 through the processor 220, or supporting the other apparatus to update at least one of the machine learning model and the modified GAN based on evaluation information about the classification information.

For example, operation S600' may include an operation of directly updating, by the computing apparatus 200, or supporting the other apparatus to update the machine learning model based on the evaluation information about the classification information or an operation of indirectly updating or supporting the other apparatus to update the machine learning model using data generated by the generator of the modified GAN by training the modified GAN based on the evaluation information about the prediction information.

Here, learning data not used for previous learning may be further considered and an error found in the previous learning may be corrected. Therefore, the accuracy of the modified GAN may be enhanced. As data accumulates, the classification performance of the machine learning model continues to improve. Also, according to example embodiments, errors in true data being provided may be significantly reduced and a class imbalance of learning data used to train the machine learning model may be solved. Therefore, the reliability of the trained machine learning model may be improved.

According to the example embodiments, although a class imbalance of learning data is high in machine learning, it is possible to enhance the accuracy of a classification model by existing machine learning through a data augmentation of generating learning data of a minority class similar to true data.

Based on the description of the example embodiments, those skilled in the art may clearly understand that the disclosure may be implemented using a combination of software and hardware or hardware alone. Targets of technical solutions of the disclosure or portions contributing to the arts may be configured in a form of program instructions performed by various computer components and stored in non-transitory computer-readable recording media. The media may include, alone or in combination with the program instructions, data files, data structures, and the like. The program instructions recorded in the media may be specially designed and configured for the example embodiments, or may be known to those skilled in the art of computer software. Examples of the media may include magnetic media such as hard disks, floppy disks, and magnetic tapes; optical media such as CD-ROM discs and DVDs; magneto-optical media such as floptical disks; and hardware devices that are specially configured to store and perform program instructions, such as ROM, RAM, flash memory, and the like. Examples of program instructions may include a machine code, such as produced by a compiler and higher language code that may be executed by a computer using an interpreter.

The hardware devices may be configured to operate as at least one software module to perform processing of the example embodiments, or vice versa. The hardware devices may include a processor, such as a CPU or a GPU, configured to combine with a memory, such as ROM/RAM, for storing program instructions and to execute the instructions stored in the memory, and may include a communicator configured to transmit and receive signals to and from an external apparatus. Further, the hardware devices may include a keyboard, a mouse, and other external input devices for receiving instructions produced by developers.

While this disclosure is described with reference to specific matters such as components, some example embodiments, and drawings, they are merely provided to help general understanding of the disclosure and this disclosure is not limited to the example embodiments. It will be apparent to those skilled in the art that various alternations and modifications in forms and details may be made from the example embodiments.

Therefore, the scope of this disclosure is not defined by the example embodiments, but by the claims and their equivalents, and all variations within the scope of the claims and their equivalents are to be construed s being included in the disclosure.

The equally or equivalent modifications may include, for example, a logically equivalent method that may achieve the same result as one acquired by implementing the method according to this disclosure.

What is claimed is:

1. A method for a computing apparatus operating based on a machine learning model, the method comprising:
   acquiring first vital signs of a subject during a first time duration;
   converting the acquired first vital signs into second vital signs that are individualized to fit a characteristic of the subject based on differences between the first vital signs and an average of vital signs for an initial partial duration of the first time duration among the first vital signs;
generating individuation data based on the individualized second vital signs;
generating analysis information about a prediction of fatal symptoms from the individuation data based on the machine learning model; and
generating the prediction result which is determined by a result of predicting occurrence of the fatal symptoms during a predetermined duration based on the analysis information.

2. The method of claim 1, further comprising:
updating the machine learning model based on evaluation information about the prediction result.

3. The method of claim 1, wherein the first vital signs are acquired from an electronic medical record (EMR) of the subject.

4. The method of claim 1, wherein
the individuation data is generated by;
generating individuation data for the subject by calculating a standard score (z-score) for the second vital signs with reference to an average and variance of vital signs of other subjects.

5. The method of claim 1, wherein the machine learning model comprises an analysis model comprising a recurrent neural network model as an analysis model,
the recurrent neural network model follows st=f(Uxt+Wst−1) and y=g(Vst),
where the xt denotes the individuation data that is an input vector at the point in time t or a value processed from the individuation data,
the st denotes a hidden state corresponding to a memory of the recurrent neural network model at the point in time t,
the st−1 denotes the hidden state at the point in time t−1,
the U, V, and W denote neural network parameters shared equally across all the points in times of the recurrent neural network model,
the f denotes a predetermined first activation function that is selected to calculate the hidden state,
the y denotes an output layer that is a latent feature according to the recurrent neural network model at the point in time t as the analysis information, and
the g denotes a predetermined second activation function that is selected to calculate the output layer, and
the machine learning model further comprises a prediction model comprising at least one fully connected layer for calculating an occurrence probability of the fatal symptoms from the output layer.

6. The method of claim 1, wherein the fatal symptoms comprise an occurrence of cardiac arrest or sepsis.

7. A non-transitory computer-readable storage medium storing a program instructions that is executable by a computer to perform the method of claim 1.

8. The method of claim 1, further comprising:
providing the generated prediction result to an external entity.

9. A computing apparatus operating based on a machine learning model, the computing apparatus comprising:
a communicator; and
a processor configured to communicate through the communicator,
wherein the processor is configured to:
acquire first vital signs of a subject during a first time duration,
convert the acquired first vital signs into second vital signs that are individualized to fit a characteristic of the subject based on differences between the first vital signs and an average of vital signs for an initial partial duration of the first time duration among the first vital signs,
generate individuation data based on the individualized second vital signs,
generate analysis information about a prediction of the fatal symptoms from the individuation data based on the machine learning model, and
generate the prediction result determined by a result of predicting occurrence of the fatal symptoms during a duration based on the analysis information.

10. The apparatus of claim 9, wherein the processor is configured to update the machine learning model based on evaluation information about the prediction result.

11. The apparatus of claim 9, wherein the machine learning model comprises:
an analysis model comprising a recurrent neural network model; and
a prediction model,
wherein the recurrent neural network model follows st=f(Uxt+Wst−1) and y=g(Vst),
where the xt denotes the individuation data that is an input vector at the point in time t or a value processed from the individuation data,
the st denotes a hidden state corresponding to a memory of the recurrent neural network model at the point in time t,
the st−1 denotes the hidden state at the point in time t−1,
the U, V, and W denote neural network parameters shared equally across all the points in times of the recurrent neural network model,
the f denotes a predetermined first activation function that is selected to calculate the hidden state,
the y denotes an output layer that is a latent feature according to the recurrent neural network model at the point in time t as the analysis information, and
the g denotes a predetermined second activation function that is selected to calculate the output layer,
wherein the prediction model comprising at least one fully connected layer for calculating an occurrence probability of the fatal symptoms from the output layer.

12. The apparatus of claim 9, wherein the fatal symptoms comprise an occurrence of cardiac arrest or sepsis.

13. A method for a computing apparatus operating based on a machine learning model, the method comprising:
acquiring vital signs of a subject during a first time duration;
converting the acquired first vital signs into second vital signs that are individualized to fit a characteristic of the subject based on differences between the first vital signs and an average of vital signs for an initial partial duration of the first time duration among the first vital signs;
generating individuation data based on the individualized second vital signs;
generating analysis information about a prediction of fatal symptoms using the individuation data based on the machine learning model; and
generating the prediction result for the first time duration,
wherein the prediction result is determined by a result of predicting occurrence of the fatal symptoms during a second time duration based on the analysis information,
wherein the second time duration is from a point in time t corresponding to a single specific vital sign among the first vital signs to a point in time t+n that is a point in time after a desired time interval n.

\* \* \* \* \*